(12) United States Patent
Chen et al.

(10) Patent No.: US 12,287,387 B2
(45) Date of Patent: Apr. 29, 2025

(54) METHOD OF USING NC-MRA TO GENERATE PELVIC VEINS IMAGES AND MEASURE RATE OF BLOOD FLOW

(71) Applicants: Chien-Wei Chen, Puzi (TW); Yao-Kuang Huang, Puzi (TW); Chung-Yuan Lee, Puzi (TW); Yeh-Giin Ngo, Puzi (TW); Yin-Chen Hsu, Puzi (TW)

(72) Inventors: Chien-Wei Chen, Puzi (TW); Yao-Kuang Huang, Puzi (TW); Chung-Yuan Lee, Puzi (TW); Yeh-Giin Ngo, Puzi (TW); Yin-Chen Hsu, Puzi (TW)

(73) Assignee: Chang Gung Memorial Hospital, Chiayi, Chiayi (TW)

( * ) Notice: Subject to any disclaimer, the term of this patent is extended or adjusted under 35 U.S.C. 154(b) by 150 days.

(21) Appl. No.: 17/901,070

(22) Filed: Sep. 1, 2022

(65) Prior Publication Data

US 2024/0077564 A1    Mar. 7, 2024

(51) Int. Cl.
| | | |
|---|---|---|
| *G01R 33/563* | (2006.01) | |
| *A61B 5/055* | (2006.01) | |
| *G01R 33/567* | (2006.01) | |

(52) U.S. Cl.
CPC .......... *G01R 33/5635* (2013.01); *A61B 5/055* (2013.01); *G01R 33/56308* (2013.01); *G01R 33/5673* (2013.01)

(58) Field of Classification Search
None
See application file for complete search history.

(56) References Cited

U.S. PATENT DOCUMENTS

2023/0003817 A1*   1/2023   Miyazaki ........... G01R 33/5602

OTHER PUBLICATIONS

Chen et al., "Usefulness of triggered non-contrast-enhanced magnetic resonance angiography in assessing lower extremity venous disease", Medicine (Baltimore), pp. 1-9, Published online May 21, 2021. (Year: 2021).*

Nagayama et al., "Non-contrast-enhanced MR Angiography with balanced turbo field echo (b-TFE) sequence: Comparison of source images, full MIP, and Parallel MIP", Proc. Intl. Soc. Mag. Reson. Med., 10, 2002. (Year: 2002).*

(Continued)

*Primary Examiner* — Katherine L Fernandez

(57) ABSTRACT

A method of using non-contrast magnetic resonance angiography (NC-MRA) to generate pelvic veins images and measure rate of blood flow includes the ordered steps of: (a) performing a non-contrast magnetic resonance scan in cooperation with an electrocardiogram monitor and a respiration monitor; (b) obtaining two-dimensional images of kidney veins, lower cavity veins, common iliac veins, and external iliac veins using use balanced turbo field echo wave sequence; (c) obtaining three-dimensional images of common cardinal veins of the abdominal cavity using fast spin-echo short tau inversion recovery wave sequence and using sample signals from the electrocardiogram monitor during myocardial contractility; and (d) using quantification phase-contrast analysis to measure blood flowing through the transverse sections of the veins in a two-dimensional scan.

6 Claims, 5 Drawing Sheets

(56) References Cited

OTHER PUBLICATIONS

Klein et al., "Magnetic resonance imaging measurement of blood vol. flow in peripheral arteries in healthy subjects", Journal of Vascular Surgery, vol. 38, No. 5, pp. 1060-1066, Nov. 2003. (Year: 2003).*

Gutzeit et al., "ECG-Triggered Non-Contrast-Enhanced MR Angiography (TRANCE) versus Digital Subtraction Angiography (DSA) in patients with peripheral arterial occlusive disease of the lower extermities", Eur Radiol, vol. 21, 2011, pp. 1979-1987. (Year: 2011).*

Takahashi et al., "Comparison of axial and coronal acquisitions by non-contrast-enhanced renal 3D MR angiography using flow-in-time-spatial labeling inversion pulse", Magnetic Resonance Materials in Physics, Biology and Medicine, pp. 1-8, Published online Dec. 28, 2019. (Year: 2019).*

Meneses et al., "Using magnetic resonance phase-contrast velocity mapping for diagnosing pelvic congestion syndrome", Phlebology, pp. 157-161, 2011. (Year: 2011).*

Ennis et al., "Flip angle optimization for quantitative phase contrast MR imaging", Journal of Cardiovascular Magnetic Resonance, pp. 1-2, 2011. (Year: 2011).*

Ahmad et al., "MFI CSF flowmetry in evaluation of different neurological diseases", Egyptian Journal of Radiology and Nuclear Medicine, 2021, pp. 1-10. (Year: 2021).*

\* cited by examiner

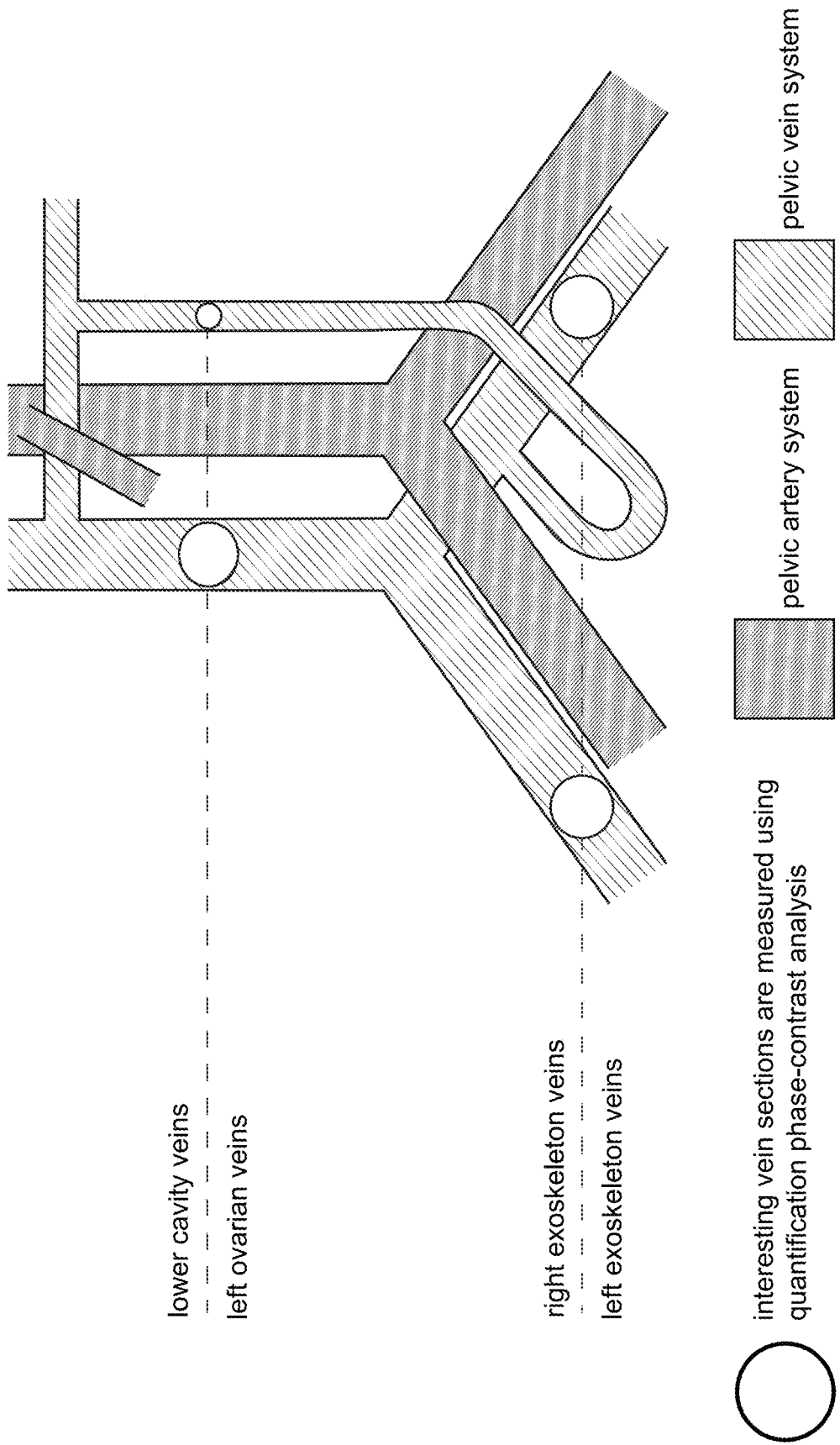

METHOD OF USING NC-MRA TO GENERATE PELVIC VEINS IMAGES AND MEASURE RATE OF BLOOD FLOW

FIELD OF THE INVENTION

The invention relates to methods of generate pelvic veins images and measure rate of blood flow and more particularly to a method of using non-contrast magnetic resonance angiography (NC-MRA) to generate pelvic veins images and measure rate of blood flow so that it is possible to evaluate pelvic veins diseases and locations of abnormal blood vessels without using developer or other medicine at a non-radiation condition, thereby increasing safety of a patient and correctness of diagnosis.

BACKGROUND OF THE INVENTION

Pelvic congestion syndrome may cause chronic pain, such as a constant dull ache. About 30% of women of reproductive age are affected by pelvic congestion syndrome. Pelvic congestion syndrome is believed to be due to blood flowing back into pelvic veins as a result of faulty valves in the veins or enlarged veins in the lower abdomen. It may be caused by venous insufficiency initially or compressed veins subsequently. In addition to chronic pain, pelvic congestion syndrome can be worsened by standing. Thus, it is important to diagnose pelvic congestion syndrome. Currently, ultrasonography, contrast-enhanced magnetic resonance angiography (CE-MRA), computed tomographic angiography (CTA) or NC-MRA is used for the diagnosis. Regarding ultrasonography, as the diagnostic tool most commonly used for diagnosing pelvic congestion syndrome, it provides dynamic information of blood flow in pelvic veins. However, ultrasonography is not capable of diagnosing specific anatomical pathology such as growth of collateral vessels. Further, its reading is subject to obesity of a patient, edema, or hip joint replacement which can adversely affect its precision. While transvaginal ultrasound can correctly diagnose pelvic congestion syndrome, it may cause pain to a patient undergoing the diagnosis. Furthermore, the examination and subsequent image reading can only be done by a professional.

Regarding CE-MRA and CTA, they can generate clear images of pelvic veins but a large amount of contrast agent is required. Further, it may have side effect or cause complication. Regarding computed tomographic, its ionizing radiation may accumulate and the accumulation may increase the risk of causing cancer to the patient. Thus, above diagnosis tools are prohibited from being used on children, pregnant women or patients having kidney disease.

Regarding NC-MRA, blood flow information can be obtained using Magnetic resonance technology without contrast agent. Thus, there is no risk of excessive ionizing radiation to the human body. However, NC-MRA is only applicable to analyses of intracranial arteries, intracranial veins, and partial examination of heart and aorta. NC-MRA has limited applications to generate pelvic veins images to evaluate pelvic congestion syndrome.

Thus, the need for improvement still exists.

SUMMARY OF THE INVENTION

It is therefore one object of the invention to provide a method of using non-contrast magnetic resonance angiography (NC-MRA) to generate pelvic veins images and measure rate of blood flow, comprising the steps of subjecting a lay patient to undergo magnetic resonance scan in cooperation with an electrocardiogram (ECG) monitor and a respiration monitor; scanning coronary sections and transverse sections of kidney veins, lower cavity veins, common iliac veins, and external iliac veins to generate two-dimensional images wherein the two-dimensional images use balanced turbo field echo wave sequence; scanning coronary sections of common cardinal veins of abdominal cavity to generate three-dimensional images wherein the three-dimensional images use fast spin-echo short tau inversion recovery wave sequence and sample signals when the ECG monitor monitors myocardial contractility; and using quantification phase-contrast analysis to measure blood flowing through the transverse sections of the veins in a two-dimensional scan.

The invention has the following advantages and benefits in comparison with the conventional art: It is a non-invasive method. Both contrast agent and ionizing radiation are not required for imaging. The generated images are useful in understanding pelvic veins and can be taken as blood dynamics information. The two-dimensional images help a medical employee to ascertain relative relationship of blood anatomy. The three-dimensional images help the medical employee to evaluate locations of abnormal blood vessels and diagnose anatomical pathology. By analyzing the measured blood flowing through the transverse sections of the veins, it is possible to determine whether the assumed symptom is true or not. Thus, a medical examination is safer and diagnosis is more precise. As an end, a medical examination of pelvic congestion syndrome and other diseases of pelvic veins are more precise, more convenient and safer.

The above and other objects, features and advantages of the invention will become apparent from the following detailed description taken with the accompanying drawings

BRIEF DESCRIPTION OF THE DRAWINGS

FIG. 5 schematically depicts how to measure a vein section using quantification phase-contrast analysis of the invention.

DETAILED DESCRIPTION OF THE INVENTION

Figure 1:
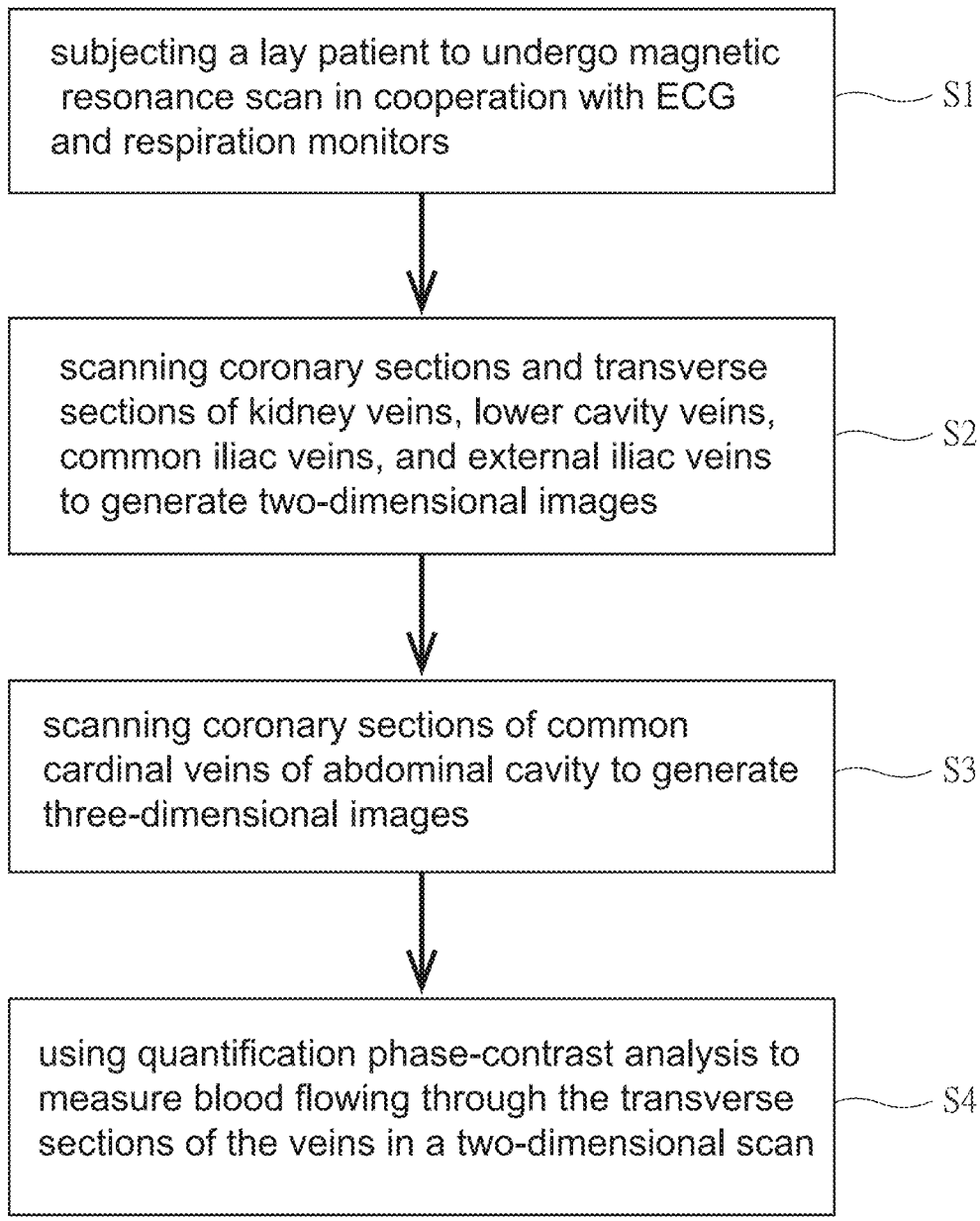
FIG. 1 is a flow chart of a method of using NC-MRA to generate pelvic veins images and measure rate of blood flow according to the invention.

Referring to FIG. 1, a method of using NC-MRA to generate pelvic veins images and measure rate of blood flow according to the invention is illustrated. The method comprises the steps of S1: subjecting a lay patient to undergo magnetic resonance scan in cooperation with an electrocardiogram (ECG) monitor and a respiration monitor;

S2: scanning coronary sections and transverse sections of kidney veins, lower cavity veins, common iliac veins and external iliac veins to generate two-dimensional images. The two-dimensional images use balanced turbo field echo wave sequence. Time for scanning coronary sections and transverse sections of kidney veins, lower cavity veins, common iliac veins and external iliac veins is about 3 minutes and 45 seconds.

S3: scanning coronary sections of common cardinal veins of abdominal cavity to generate three-dimensional images. The three-dimensional images use fast spin-echo short tau inversion recovery wave sequence and sample signals when the ECG monitor monitors myocardial contractility. Time for scanning coronary sections of common cardinal veins of abdominal cavity is about 2 minutes and 39 seconds.

S4: using quantification phase-contrast analysis to measure blood flowing through the transverse sections of the veins in a two-dimensional scan. Two planes are scanned in the two-dimensional scan and time for each scan is about 1 minute and 6 seconds.

Total scanning time is 8 minutes and 36 seconds and a complete computed tomographic angiography (CTA) is about 30 minutes.

Parameters for the two-dimensional images using the balanced turbo field echo wave sequence are as follows: two-dimensional mode, echo time=the shortest, repetition time=the shortest, pixel size=1.4×1 mm, slice thickness=7 mm, gap=3.5 mm, average number of signals=1, and fat inhibition. The balanced turbo field echo wave sequence is a gradient echo pulse sequence with a balanced gradient waveshape, and data is sampled after initial ready pulses to enhance contrast. Fat tissues are separated using fat inhibition, resulting in images with a low signal background and high signals for blood vessels and body fluids.

Parameters for acquiring three-dimensional images using the fast spin-echo short tau inversion recovery wave sequence include the following settings: three-dimensional mode, echo time=85 ms, repetition time=1 heart beat, turbo spin echo factor=37, reverse recovery delay time=160 ms, and voxel size=1.7×1.9×4 mm, using the ECG monitor to sample signals in myocardial contractility [,]. The scanning surface is a coronary surface, and the scanning area includes the common cardinal veins of the entire abdominal cavity.

Parameters of using quantification phase-contrast analysis to measure blood flowing through the transverse sections of the veins in a two-dimensional scan include two-dimensional quantification, echo time=the shortest, repetition time=the shortest, inverse angle=20 degrees, pixel size=1.6× 2.1 mm, slice thickness=6 mm, and encoding speed=120 mm/sec. Fluid flow toward the head is encoded as positive and fluid flow toward the feet is encoded as negative. The quantification phase-contrast analysis for scanning comprises four steps including (a) dividing pelvic veins, (b) obtaining time curve of the rate of blood flow of the veins, (c) accumulating and calibrating, and (d) calculating quantification parameters of the rate of blood flow of the veins. Following interesting vein sections are scanned and measured: lower cavity veins, left ovarian veins, right exoskeleton veins and left exoskeleton veins. The following quantification parameters of each analyzed vein section can be obtained: stroke quantity, forward flow, rearward flow, reverse flow fraction, absolute stroke quantity, average flux, stroke distance and average rate.

Figure 2:
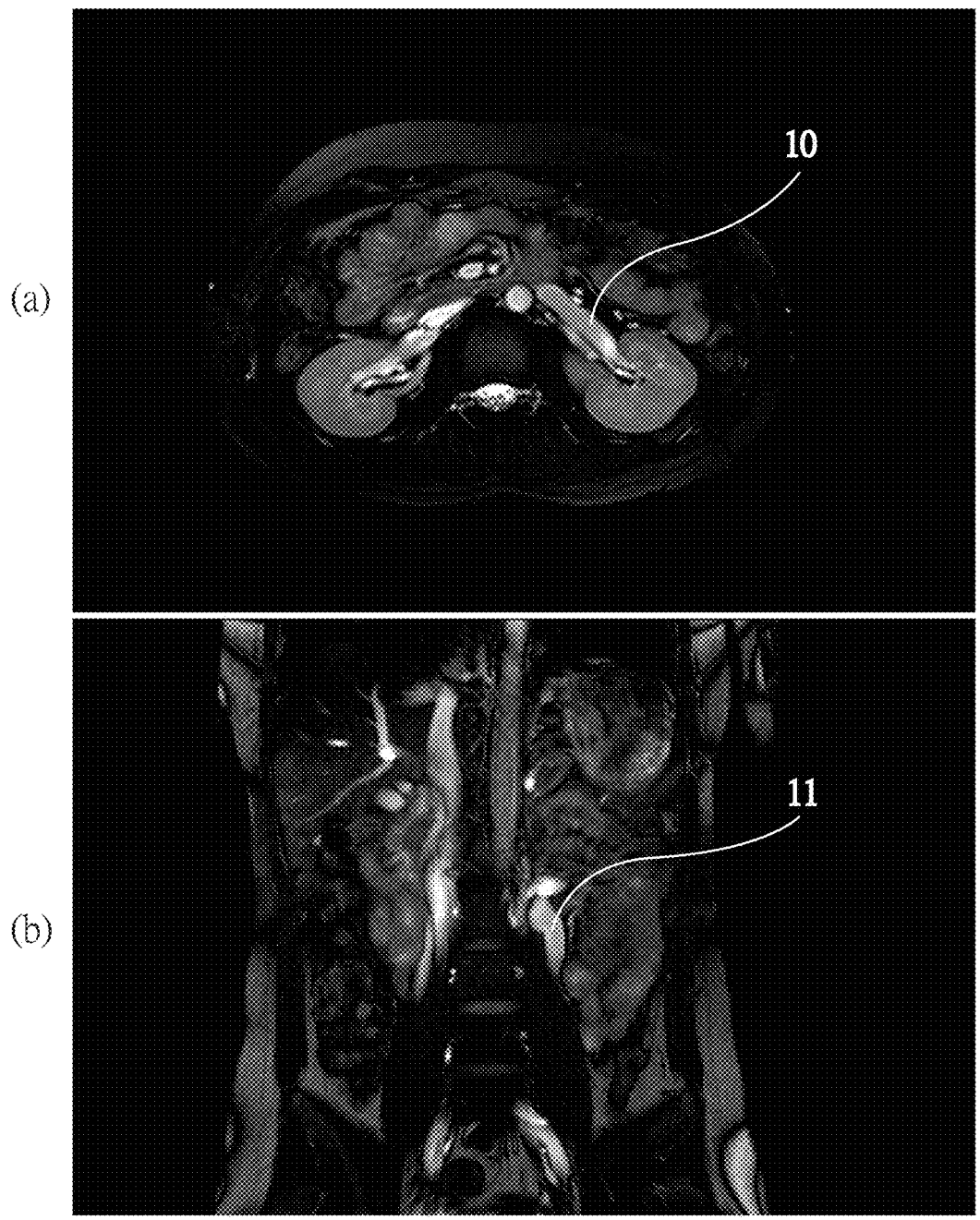
FIG. 2 shows two-dimensional images generated by the method of using NC-MRA of the invention.

Referring to FIG. 2, it shows two-dimensional images generated by the method of using NC-MRA of the invention. Clear artery and vein images are shown because the fast spin-echo short tau inversion recovery wave sequence is used and it helps a medical employee to understand relative relationship of blood anatomy. A shown in (a) of FIG. 2, an image of transverse section of blooded left kidney veins is labeled by numeral 10. As shown in (b) of FIG. 2, an image of coronary section of blooded left ovary veins is labeled by numeral 11.

Figure 3:
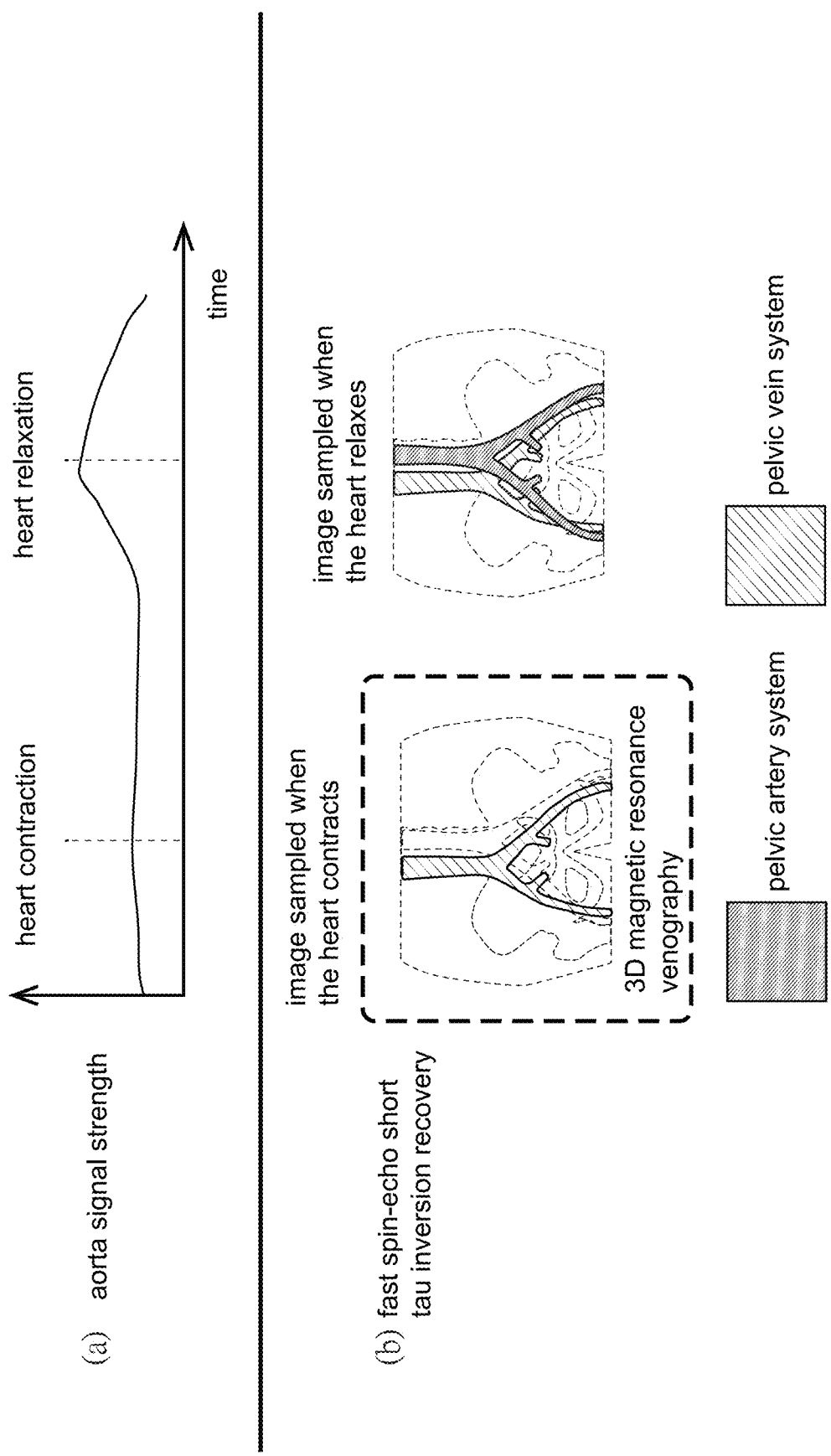
FIG. 3 schematically depicts three-dimensional images generated by means of fast spin-echo short tau inversion recovery wave sequence.

Referring to FIG. 3, it schematically depicts three-dimensional images generated by means of fast spin-echo short tau inversion recovery wave sequence. As shown in (a) of FIG. 3, it plots aorta signal strength versus time. Both the aorta signal and the vein signal are strong when the heart relaxes. The aorta signal disappears due to flow void effect of quick blood flow when the heart contracts. But the vein signal is strong when the heart contracts. Further, the aorta signal is weak when the heart contracts, but is strong when the heart relaxes.

It is possible to obtain blood vessels data by triggering sample signals in time using gated imaging acquisition technology. It is also possible to establish a three-dimensional blood vessel structure using imaging technology, i.e., three-dimensional imaging. As shown in (b) of FIG. 3, imaging is made using gated imaging acquisition technology in cooperation with the ECG monitor when the heart contracts or relaxes. Also, fast spin-echo short tau inversion recovery technology is used to inhibit signals of background (e.g., fat and bones). But three-dimensional images of only veins are generated, i.e., magnetic resonance vein angiography.

Figure 4:
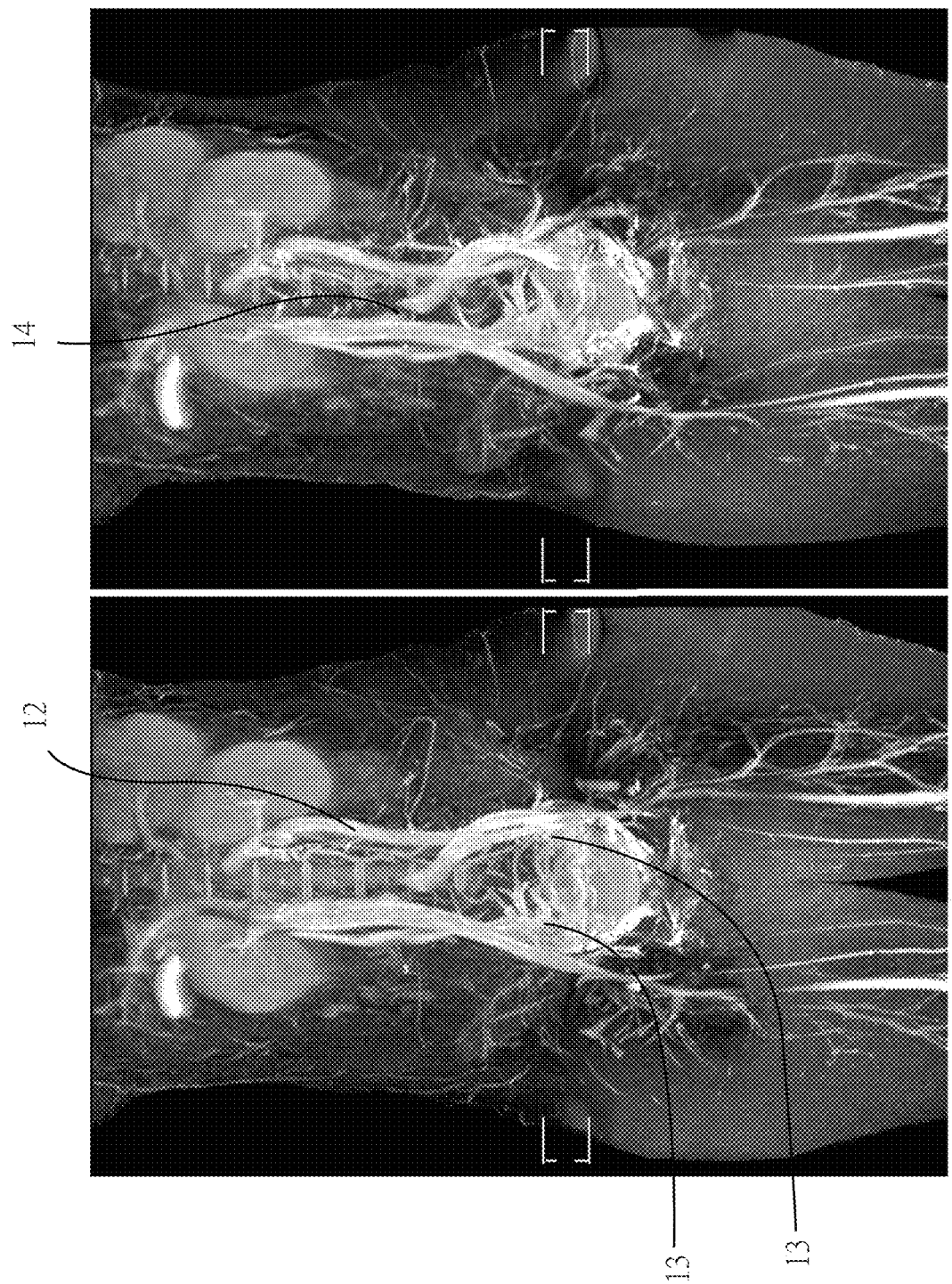
FIG. 4 schematically depicts three-dimensional images generated by means of the method of the invention.

Referring to FIG. 4, it schematically depicts three-dimensional images generated by means of the method of the invention. There is no need for imaging blood flow since fast spin-echo short tau inversion recovery wave sequence is used. Thus, images of independent vein system having a high resolution are generated. Particularly, quality images of vein compression, vein bend, and blooded veins can be generated. As shown in (a) of FIG. 4, in the plan view of pelvic, a blooded left ovary vein is labeled by numeral 12 and each of two pelvic vein bend are labeled by numeral 13. As shown in (b) of FIG. 4, in the side elevation of pelvic, a left common iliac vein compression is shown clearly and labeled by numeral 14. All of above characteristics are exemplary presentations of pelvic congestion syndrome.

Referring to FIG. 5, it schematically depicts how to measure an interesting vein section using quantification phase-contrast analysis of the invention. Core technology is the use of phase-contrast magnetic resonance Imaging. Fluid has phase shifting of different degrees due to repetitive bi-polar gradient. The greater of the fluid speed the greater of the phase shifting. Thus, it is possible to estimate fluid speed by measuring phase shifting of a target fluid. Quantification phase-contrast analysis can analyze blood dynamics models of both healthy blood and pathologic blood based on obtained data. Two images of transverse section are generated by means of phase-contrast magnetic resonance scanning. Further, phase shifting signals of pixels in four vein sections are measured to effectively establish a blood dynamics model of pelvic vein system which is capable of estimating pelvic congestion syndrome.

The invention uses quantification phase-contrast analysis to analyze 36 patients having pelvic congestion syndrome as experiment group and 10 healthy individuals as control group and analysis results are arranged in Table 1 below. As shown, there are differences among vein measurement parameters between the experiment group and the control group. Also, many measurement targets have shown significant differences in terms of statistics. Specifically, blood from left ovary veins flows back to the heart is significant for the patients having pelvic congestion syndrome. It is noted that p value less than 0.05 is marked by * in order to show there is a great difference.

TABLE 1

| Vein section | Experiment group average | Experiment group Standard deviation | Control group average | Control group Standard deviation | P value |
|---|---|---|---|---|---|
| Stroke quantity | | | | | |
| Left ovary veins | 0.79 | 1.10 | 0.96 | 0.42 | 0.637 |
| Lower cavity veins | 14.60 | 4.24 | 18.55 | 6.66 | 0.027* |
| Right exoskeleton veins | 5.51 | 2.18 | 4.29 | 1.20 | 0.029* |
| Left exoskeleton veins | 4.58 | 1.98 | 3.85 | 1.28 | 0.275 |
| Forward flow | | | | | |
| Left ovary veins | 0.31 | 0.30 | 0.89 | 0.51 | 0.006* |
| Lower cavity veins | 14.96 | 4.36 | 19.20 | 6.59 | 0.02* |
| Right exoskeleton veins | 5.62 | 2.20 | 4.45 | 1.35 | 0.303 |
| Left exoskeleton veins | 4.69 | 2.16 | 3.94 | 1.30 | 0.119 |
| Rearward flow | | | | | |
| Left ovary veins | 2.13 | 9.48 | 0.07 | 0.22 | 0.5 |
| Lower cavity veins | 0.35 | 0.96 | 0.64 | 1.13 | 0.422 |
| Right exoskeleton veins | 0.10 | 0.30 | 0.16 | 0.33 | 0.63 |
| Left exoskeleton veins | 0.10 | 0.47 | 0.09 | 0.20 | 0.904 |
| reverse flow fraction | | | | | |
| Left ovary veins | 12.87 | 22.37 | 0.00 | 0.00 | 0.001* |
| Lower cavity veins | 2.21 | 5.24 | 3.35 | 5.83 | 0.555 |
| Right exoskeleton veins | 1.95 | 5.41 | 2.81 | 5.30 | 0.66 |
| Left exoskeleton veins | 1.45 | 4.71 | 1.97 | 4.83 | 0.758 |
| absolute stroke quantity | | | | | |
| Left ovary veins | 0.87 | 1.06 | 0.96 | 0.42 | 0.793 |
| Lower cavity veins | 15.31 | 4.68 | 19.84 | 6.72 | 0.018* |
| Right exoskeleton veins | 5.72 | 2.20 | 4.61 | 1.56 | 0.146 |
| Left exoskeleton veins | 4.79 | 2.42 | 4.02 | 1.36 | 0.343 |
| Average flux | | | | | |
| Left ovary veins | 0.95 | 1.36 | 1.02 | 0.48 | 0.874 |
| Lower cavity veins | 17.50 | 5.87 | 19.95 | 8.49 | 0.296 |
| Right exoskeleton veins | 6.30 | 2.78 | 4.31 | 1.25 | 0.003* |
| Left exoskeleton veins | 5.17 | 2.18 | 3.86 | 1.29 | 0.078 |
| Stroke distance | | | | | |
| Left ovary veins | −0.37 | 3.01 | 3.36 | 2.81 | 0.001* |
| Lower cavity veins | 8.92 | 2.88 | 12.76 | 7.40 | 0.14 |
| Right exoskeleton veins | 5.81 | 2.06 | 4.44 | 1.42 | 0.054 |
| Left exoskeleton veins | 5.18 | 1.75 | 3.65 | 1.12 | 0.013* |
| Average rate | | | | | |
| Left ovary veins | −0.46 | 3.62 | 3.53 | 3.14 | 0.003* |
| Lower cavity veins | 13.34 | 7.01 | 13.34 | 7.01 | 0.266 |
| Right exoskeleton veins | 6.59 | 2.37 | 4.43 | 1.28 | 0.008* |
| Left exoskeleton veins | 5.89 | 2.09 | 3.65 | 1.04 | 0.002* |

The invention uses NC-MRA and ultrasound scan to analyze 46 patients having pelvic congestion syndrome and analysis results are arranged in Table 2 below.

TABLE 2

| | Positive in ultrasound scan | Negative in ultrasound scan |
|---|---|---|
| Positive in NC-MRA | 29 (TP) | 1 (FP) |
| Negative in NC-MRA | 7 (FN) | 9 (TN) |

In Table 2, true positive (TP) means both ultrasound scan and NC-MRA are positive; false positive (FP) means ultrasound scan is negative and NC-MRA is positive; false negative (FN) means ultrasound scan is positive and NC-MRA is negative; and true negative (TN) means both ultrasound scan and NC-MRA are negative.

Further, TP, FP, TN and FN are substituted into expressions of Table 3 and results are arranged in Table 3 below.

TABLE 3

| | Value % | expression |
|---|---|---|
| Sensitivity (TPR) | 80.6% | TPR = TP/(TP + FN) |
| Specificity (SPC) | 90% | SPC = TN/(FP + TN) |
| Precision (PPV) | 96.7% | PPV = TP/(TP + FP) |
| Negative Predictive Value (NPV) | 56.3% | NPV = TN/(TN + FN) |
| False Positive Rate (FPR) | 3% | FPR = FP/(FP + TN) |
| False Discovery Rate (FDR) | 4% | FDR = FP/(FP + TP) |
| False Negative Rate (FNR) | 19.4% | FNR = FN/(FN + TP) |
| Accuracy (ACC) | 82.6% | ACC = (TP + TN)/(TP + TN + FP + FN) |

In Table 3, sensitivity, specificity and accuracy of pelvic congestion syndrome are 80.6%, 90% and 82.6% respectively. Inter-rater agreement shows Cohen's Kappa is 0.58 so that it is a moderate agreement.

In view of Tables 1, 2 and 3, it is concluded that the method of the invention can effectively evaluate pelvic veins and correctly diagnose pelvic congestion syndrome.

It is envisaged by the invention that balanced turbo field echo wave sequence is utilized to generate the two-dimensional images, fast spin-echo short tau inversion recovery wave sequence is utilized to generate the three-dimensional images, and quantification phase-contrast analysis is utilized to measure blood flowing through transverse sections of the veins. Different signals can be obtained from the three-dimensional images by processing different rates of blood flow between the heart contraction and the heart relaxation. Then images obtained at the heart relaxation are subtracted from image obtained at the heart contraction to eliminate signals of the arteries, the bones and the body tissues by means of silhouette technique. As a result, clear three-dimensional images are generated.

While the invention has been described in terms of preferred embodiments, those skilled in the art will recognize that the invention can be practiced with modifications within the spirit and scope of the appended claims.

What is claimed is:

1. A method for using non-contrast magnetic resonance angiography (NC-MRA) to generate images of a patient's pelvic veins and measure rate of blood flow for diagnosing and evaluating pelvic congestion syndrome in women of reproductive age, the method comprising the ordered steps of:
    (a) performing a non-contrast magnetic resonance scan on the patient using an electrocardiogram (ECG) monitor and a respiration monitor for the pelvic congestion syndrome evaluation, the patient having kidney veins, lower cavity veins, common iliac veins, external iliac veins, and an abdominal cavity having common cardinal veins, the patient having pelvic veins consisting of lower cavity veins, left ovarian veins, right exoskeleton veins, and left exoskeleton veins;

(b) obtaining two-dimensional images of the kidney veins, the lower cavity veins, the common iliac veins, and the external iliac veins using a balanced turbo field echo wave sequence;

(c) obtaining three-dimensional images of the common cardinal veins of the abdominal cavity using a fast spin-echo short tau inversion recovery wave sequence and using sample signals from the ECG monitor during myocardial contractility; and (d) using quantification phase-contrast magnetic resonance analysis to measure blood flow through transverse sections of the pelvic veins in a two-dimensional scan, wherein:

the quantification phase-contrast magnetic resonance analysis comprises the steps of dividing the pelvic veins, obtaining a time curve of the rate of blood flow of the pelvic veins, and obtaining quantification parameters of the rate of blood flow of the pelvic veins, wherein the quantification parameters of the pelvic veins comprise stroke quantity, forward flow, rearward flow, reverse flow fraction, absolute stroke quantity, average flux, stroke distance and average rate; and phase shifting signals for the lower cavity veins, the left ovarian veins, the right exoskeleton veins, and the left exoskeleton veins are measured to establish a blood dynamics model of the pelvic veins.

2. The method of claim 1, wherein a plurality of parameters of the two-dimensional images of the kidney veins, the lower cavity veins, the common iliac veins, and the external iliac veins using the balanced turbo field echo wave sequence are optimized for the pelvic congestion syndrome evaluation, including two-dimensional mode, echo time, repetition time, pixel size, slice thickness, gap, average number of signals, and fat inhibition.

3. The method of claim 1, wherein a plurality of parameters of the three-dimensional images of the common cardinal veins of the abdominal cavity using the fast-spin echo short tau inversion recovery wave sequence are specifically configured for pelvic vein visualization in pelvic congestion syndrome diagnosis, including three-dimensional mode, echo time, repetition time, turbo spin echo factor, reverse recovery delay time, and voxel size.

4. The method of claim 1, wherein a plurality of parameters of using the quantification phase-contrast analysis optimized for the pelvic congestion syndrome diagnosis include two-dimensional quantification, echo time, repetition time, inverse angle, pixel size, slice thickness, and encoding speed.

5. The method of claim 1, wherein the sample signals from the ECG monitor are sampled by means of gated imaging acquisition technology optimized for the pelvic congestion syndrome diagnosis to ensure accurate blood flow measurement in pelvic veins during different cardiac phases.

6. The method of claim 1, wherein the period of time spent performing the non-contrast magnetic resonance scan on the common cardinal veins is less than a period of time spent performing the non-contrast magnetic resonance scan on the kidney veins, the lower cavity veins, the common iliac veins, and the external iliac veins.

* * * * *